United States Patent
Kim et al.

(10) Patent No.: US 11,441,143 B2
(45) Date of Patent: Sep. 13, 2022

(54) ENZYME-CARRIER COMPLEX

(71) Applicant: Korea University Research and Business Foundation, Seoul (KR)

(72) Inventors: Jungbae Kim, Seoul (KR); Tae Hee Kim, Seoul (KR)

(73) Assignee: Korea Univercity Research and Business Foundation, Seoul (KR)

(*) Notice: Subject to any disclaimer, the term of this patent is extended or adjusted under 35 U.S.C. 154(b) by 0 days.

(21) Appl. No.: 17/119,473

(22) Filed: Dec. 11, 2020

(65) Prior Publication Data

US 2021/0115432 A1    Apr. 22, 2021

Related U.S. Application Data

(63) Continuation of application No. PCT/KR2020/001530, filed on Jan. 31, 2020.

(30) Foreign Application Priority Data

Jan. 31, 2019 (KR) .................. 10-2019-0012434

(51) Int. Cl.
   *C12N 11/14* (2006.01)
   *C12N 9/96* (2006.01)

(52) U.S. Cl.
   CPC .............. *C12N 11/14* (2013.01); *C12N 9/96* (2013.01); *C12Y 305/01004* (2013.01)

(58) Field of Classification Search
   CPC ......... C12N 11/02; C12N 11/06; C12N 11/08; C12N 11/082; C12N 11/084; C12N 11/087; C12N 11/089; C12N 11/091; C12N 11/093; C12N 11/096; C12N 11/098; C12N 11/14; C12N 11/96; C12N 9/78; C12N 9/80
   See application file for complete search history.

(56) References Cited

U.S. PATENT DOCUMENTS 7,611,835 B2 * 11/2009 Kim .................. C12N 9/6427
                                                    435/176

FOREIGN PATENT DOCUMENTS

| CN | 105836731 A | | 8/2016 |
|---|---|---|---|
| CN | 106636058 A | * | 5/2017 |
| CN | 106676092 A | * | 5/2017 |
| KR | 10-1995-0008685 A | | 4/1995 |
| KR | 10-0351887 B1 | | 11/2002 |
| KR | 10-2011-0128134 A | | 11/2011 |
| KR | 10-2016-0092652 A | | 8/2016 |
| WO | 79/00875 A1 | | 11/1979 |

OTHER PUBLICATIONS

Basso et al., "Industrial applications of immobilized enzymes—A review", Molecular Catalysis 479 (2019) 110607 (Year: 2019).*
U.S. Appl. No. 17/118,814, filed 2020.*
Byoung Chan Kim et al., "Fabrication of enzyme-based coatings on intact multi-walled carbon nanotubes as highly effective electrodes in biofuel cells", Scientific Reports, 2017, pp. 1-10, vol. 7, 40202.
Tae Hee Kim et al., "Biocatalytic membrane with acylase stabilized on intact carbon nanotubes for effective antifouling via quorum quenching", Journal of Membrane Science, 2018, pp. 357-365, vol. 554.
International Search Report for PCT/KR2020/001530, dated Jun. 19, 2020.

* cited by examiner

*Primary Examiner* — Ruth A Davis
(74) *Attorney, Agent, or Firm* — Sughrue Mion, PLLC

(57) ABSTRACT

The present invention relates to an enzyme-carrier complex, and more particularly to the adsorption and stabilization of an enzyme on the surface of a carrier, and an enzyme-carrier complex with secured enzyme stability so that an enzyme immobilized by a hydrophobic interaction exhibits long-term enzymatic activity.

8 Claims, 3 Drawing Sheets

ENZYME-CARRIER COMPLEX

CROSS REFERENCE TO RELATED APPLICATIONS

This application is a continuation application of, and claims priority from International Application No. PCT/KR2020/001530 filed Jan. 31, 2020, claiming priority from Korean Patent Application No. 10-2019-0012434 filed Jan. 31, 2019, the entire disclosures of which are incorporated herein by reference.

TECHNICAL FIELD

The present invention relates to an enzyme-carrier complex, and more particularly to the adsorption and stabilization of an enzyme on the surface of a carrier, and an enzyme-carrier complex with secured enzymatic stability so that an enzyme immobilized by a hydrophobic interaction exhibits long-term enzymatic activity.

BACKGROUND ART

Enzymes have the characteristics of high ultra-precision, specificity, selectivity, and high efficiency, and thus the use thereof is expanding to various industries run by humans, and in terms of function, enzymes not only have the general function of catalyzing redox, transition, hydrolysis, desorption and addition, isomerization, and synthesis reactions, but also have the characteristic of catalyzing reactions under special conditions such as high temperature, high pressure, and organic solvents, and thus an industrially application range thereof is unlimited, and accordingly, utilization thereof as a future industrial material is very high.

However, enzymes are easily structurally denatured by external environments such as heat and pH, and thus there is a problem that application thereof is highly limited due to the instability of enzymatic activity. In order to address this problem, recently, research on gene recombination technology or enzyme immobilization technology has been actively conducted to enhance the stability of an enzyme.

With regard to the enzyme immobilization technology, a technique for modifying the surface of a carrier with a functional group capable of binding to an enzyme, and then immobilizing the enzyme on the carrier through covalent bonding via the functional group is actively being researched. When this method is used, stable binding can be ensured, but there is a problem that the activity of an enzyme to be immobilized is deteriorated or lost due to structural denaturation of the enzyme occurring during a reaction for covalent bonding. In addition, there is a disadvantage that an additional functionalization process is required to modify the surface of a carrier so as to have a functional group, and in such a functionalization process, the intrinsic properties of a carrier may be changed or deteriorated.

Therefore, there is an urgent need for an enzyme immobilization technique which is able to immobilize an enzyme on a carrier while minimizing the deterioration of enzymatic activity, maintain long-term enzymatic activity, and minimize the deterioration of intrinsic properties of the carrier due to modification.

DESCRIPTION OF EMBODIMENTS

Technical Problem

The present invention has been made in view of the above problems, and it is an object of the present invention to provide an enzyme-carrier complex in which an enzyme is immobilized on a carrier while the deterioration of enzymatic activity is minimized, that is able to secure enzyme stability so that long-term enzymatic activity is exhibited, and that is able to minimize the deterioration of intrinsic properties of a carrier.

Also, it is another object of the present invention is to provide an enzyme-carrier complex capable of securing dispersibility in an aqueous solution.

Technical Solution

According to an aspect of the present invention, there is provided an enzyme-carrier complex including a hydrophobic carrier and an enzyme adsorbed on a surface of the hydrophobic carrier.

According to one embodiment of the present invention, the enzyme may include one or more enzymes selected from the group consisting of acylase, trypsin, chymotrypsin, pepsin, lipases, glucose oxidase, pyranose oxidase, horseradish peroxidase, thyroxinase, carbonic anhydrase, formaldehyde dehydrogenase, formate dehydrogenase, alcohol dehydrogenase, cholesterol dehydrogenase, lactonase, proteases, peroxidases, aminopeptidases, phosphatases, transaminases, serine-endopeptidase, cysteine-endopeptidase, and metalloendopeptidases.

In addition, the hydrophobic carrier may include one or more materials selected from the group consisting of carbon nanotubes, fullerenes, graphene, porous carbon, polycarbonate, polyimide, polystyrene, polydimethylsiloxane, and polyethylene terephthalate.

In addition, the hydrophobic carrier may further include a first functional group on a surface thereof to induce a hydrophobic interaction with the enzyme.

In addition, the enzyme may further include a second functional group for inducing a hydrophobic interaction with the first functional group.

In this regard, the second functional group for inducing a hydrophobic interaction may include one or more functional groups selected from the group consisting of a halogenated alkyl group, an organosilicon group, an alkyl group, a vinyl group, an allyl group, and an aryl group.

In addition, the enzyme-carrier complex may be any one selected from the group consisting of an acylase-carbon nanotube complex, a trypsin-carbon nanotube complex, a lipase-carbon nanotube complex, a glucose oxidase-carbon nanotube complex, a pyranose oxidase-carbon nanotube complex, a horseradish peroxidase-carbon nanotube complex, a tyrosinase-carbon nanotube complex, a carbonic anhydrase-carbon nanotube complex, and a formaldehyde dehydrogenase-carbon nanotube complex.

The present invention also provides an electrode for a biofuel cell including the enzyme-carrier complex according to the present invention.

The present invention also provides an electrode for a biosensor including the enzyme-carrier complex according to the present invention.

The present invention also provides a carbon dioxide conversion system including the enzyme-carrier complex according to the present invention.

The present invention also provides an anti-fouling system including the enzyme-carrier complex according to the present invention.

Advantageous Effects of Invention

An enzyme-carrier complex according to the present invention enables an enzyme to be stably immobilized on a carrier without denaturation of the active site of the enzyme, and after immobilization, can exhibit long-term enzymatic activity. In addition, even after the immobilization of an enzyme on a carrier, deterioration of the intrinsic properties of the carrier can be minimized, and thus it is advantageous in that the intrinsic properties of the carrier are fully exhibited. Moreover, even when the carrier has hydrophobic properties, it is possible to secure dispersibility in an aqueous solution, and thus it is suitable for use in various applications requiring long-term stable enzyme performance. In addition, without using components having a biocompatibility problem, such as a crosslinking agent, which have been applied to an enzyme stabilization technique, the enzyme is immobilized and stabilized, and thus use of the enzyme-carrier complex can be expanded to the medical field where use of such components is limited.

Accordingly, when the enzyme-carrier complex is used in the immobilization of related enzymes, such as glucose oxidase and pyranose oxidase, in order to manufacture glucose-based biofuel cells and biosensors for measuring blood glucose, a very high stabilization effect can be achieved. In addition, when the enzyme-carrier complex is used in the immobilization of related enzymes, such as carbonic anhydrase capable of converting carbon dioxide into bicarbonate and formate dehydrogenase capable of converting bicarbonate into formic acid, it is possible to stably maintain activity for a long time without denaturation of an enzyme, compared to conventional immobilization methods using a crosslinking agent, and thus the enzyme-carrier complex can be used as a catalyst material for a carbon dioxide conversion and utilization system. In addition, when the enzyme-carrier complex is used in the immobilization of related enzymes such as acylase which is able to inhibit biofilm formation by decomposing a signaling molecule that performs a quorum sensing function, the activity of an enzyme can be stably maintained without denaturation thereof compared to conventional immobilization methods using a crosslinking agent and accordingly, the enzyme-carrier complex can be used as a catalyst material in an antifouling system to suppress the formation of a biofilm on the surface of a membrane. The enzyme-carrier complex can also be used in various applications such as electrochemical and pharmaceutical industries in addition to the above-listed examples.

BEST MODE

Hereinafter, embodiments of the present invention will be described in detail in such a manner that the invention can be carried out by one of ordinary skill in the art to which the present invention pertains, without undue difficulty. The present invention may be embodied in many different forms and is not limited by embodiments set forth herein.

Figure 1:
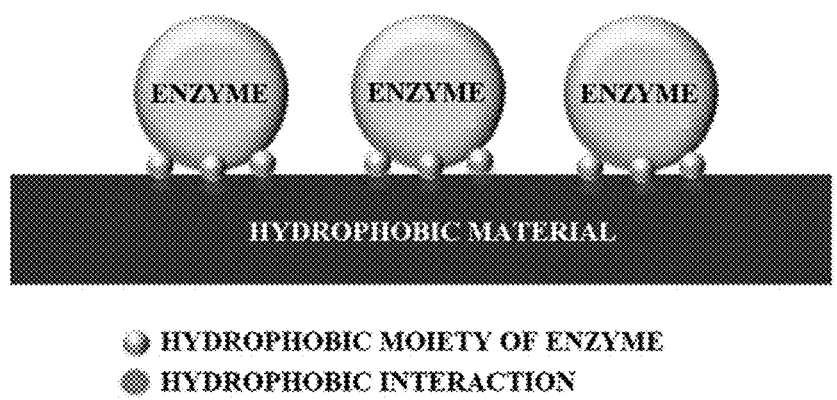
FIG. 1 is a view of an enzyme-carrier complex according to an embodiment of the present invention.

Referring to FIG. 1, an enzyme-carrier complex according to the present invention includes a hydrophobic carrier and an enzyme adsorbed on a surface of the hydrophobic carrier. In one embodiment, the absorption may occur by a hydrophobic interaction between a hydrophobic moiety of the enzyme and the surface of the hydrophobic carrier.

Any hydrophobic carrier may be used without limitation as long as it is an insoluble material that is commonly referred to as exhibiting hydrophobicity in the art. In the present invention, the hydrophobic carrier refers to a carrier capable of having a van der Waals interaction or a pi-pi interaction, among non-covalent bonds, with the surface of the enzyme on the surface thereof that can contact the surface of the enzyme. In addition, any hydrophobic carrier may be used without limitation as long as it is a material as defined above, and may include, for example, one or more materials selected from the group consisting of carbon nanotubes, fullerenes, graphene, porous carbon such as nanoporous carbon or activated carbon, polycarbonate, polyimide, polystyrene, polydimethylsiloxane, and polyethylene terephthalate.

The shape of the hydrophobic carrier is not limited, and may be, for example, one or more shapes selected from the group consisting of spherical, plate, rod, tubular, and amorphous shapes. In addition, the hydrophobic carrier may further include nano-sized pores in the surface thereof, but the present invention is not limited thereto.

In addition, the size of the hydrophobic carrier may vary from nanoscale to microscale, but the present invention is not particularly limited thereto.

In addition, the hydrophobic carrier may further include, on the surface thereof, a first functional group to induce a hydrophobic interaction with the enzyme or to further enhance the hydrophobic interaction. The hydrophobic interaction minimizes or prevents an effect on the steric structure of an enzyme compared to covalent bonding, and thus is advantageous in that it can prevent or minimize problems such as denaturation of the steric structure of an enzyme and deterioration or loss of enzymatic activity, which occur according to strong binding affinity caused when an enzyme is immobilized on a support via conventional covalent bonding or when enzymes are crosslinked via covalent bonding. In this regard, the first functional group included in the hydrophobic carrier is not limited as long as it is a functional group capable of inducing a hydrophobic interaction, and may include, for example, one or more functional groups selected from the group consisting of a halogenated alkyl group, an organosilicon group, an alkyl group, a vinyl group, an allyl group, and an aryl group.

In addition, the first functional group may be introduced onto the surface of the hydrophobic carrier through a known technique, but the present invention is not particularly limited thereto.

As the enzyme, any known enzyme may be employed without limitation, and may include, for example, one or more enzymes selected from the group consisting of acylase, trypsin, chymotrypsin, pepsin, lipases, glucose oxidase, pyranose oxidase, horseradish peroxidase, thyroxinase, carbonic anhydrase, formaldehyde dehydrogenase, formate dehydrogenase, alcohol dehydrogenase, cholesterol dehydrogenase, lactonase, proteases, peroxidases, aminopeptidases, phosphatases, transaminases, serine-endopeptidase, cysteine-endopeptidase, and metalloendopeptidases. More preferably, the enzyme may include one or more selected from the group consisting of acylase, trypsin, lipases, glucose oxidase, pyranose oxidase, horseradish peroxidase, thyroxinase, carbonic anhydrase, and formaldehyde dehydrogenase, and even more preferably, the enzyme may be acylase.

In addition, according to one embodiment of the present invention, the enzyme may further include a second functional group for enhancing a hydrophobic interaction with the hydrophobic carrier. The second functional group may function to minimize the effect on the steric structure of the enzyme while minimizing dissociation of the enzyme from the hydrophobic carrier, and stably exhibit enzymatic activity. The second functional group may include one or more functional groups selected from the group consisting of a halogenated alkyl group, an organosilicon group, an alkyl group, a vinyl group, an allyl group, and an aryl group. In addition, the second functional group may be selected from those that are the same as or different from the first functional group that may be included in the hydrophobic carrier, but the present invention is not particularly limited thereto.

According to one embodiment of the present invention, the enzyme and the hydrophobic carrier in the above-described enzyme-carrier complex may be any one combination selected from an acylase-carbon nanotube complex, a trypsin-carbon nanotube complex, a lipase-carbon nanotube complex, a glucose oxidase-carbon nanotube complex, a pyranose oxidase-carbon nanotube complex, a horseradish peroxidase-carbon nanotube complex, a tyrosinase-carbon nanotube complex, a carbonic anhydrase-carbon nanotube complex, and a formaldehyde dehydrogenase-carbon nanotube complex, and due to an enhanced interaction between the enzyme and the surface of the carrier in such a combination, the enzyme may be stably immobilized, and there is an advantage that long-term enzymatic activity may be exhibited.

Mode of Invention

Hereinafter, the present invention will be described in detail with reference to the following examples. However, these examples are not intended to limit the scope of the present invention.

Example 1>—Preparation of Enzyme-Carrier Complex Using Acylase and Carbon Nanotubes (ADS-AC/CNTs)

A carbon nanotube (CNT) solution (8 mg/mL) and an acylase (AC) solution (40 mg/mL), prepared using phosphate-buffered saline (100 mM, pH 7.0) as a solvent, were mixed in the same volume ratio, followed by stirring at 200 rpm for 1 hour to thereby adsorb acylase onto the surfaces of carbon nanotubes. Subsequently, acylase unattached to the carbon nanotubes was removed using phosphate-buffered saline, followed by stirring with Tris buffer (100 mM, pH 7.4) at 200 rpm for 30 minutes, causing unreacted functional groups to be capped. Thereafter, the prepared enzyme-carrier complex was centrifuged to remove the supernatant, washed with phosphate-buffered saline, and then stored at 4° C.

<Comparative Example 1>—Free Acylase Solution (Free AC)

An acylase solution dissolved in phosphate-buffered saline (100 mM, pH 7.0) was prepared.

<Experimental Example 1> Measurement of Enzymatic Activity and Stability of Enzyme-Carrier Complex Using Acylase and Carbon Nanotubes As an enzyme, acylase (AC), which decomposes bacterial quorum-sensing signaling material, was used. AC activity was measured using fluorescence emitted as a result of reaction of L-methionine produced by hydrolysis of N-acetyl-L-methionine with o-phthalaldehyde (OPA).

Enzyme stability was evaluated by measuring a decrease in enzymatic activity while continuing to stir at 200 rpm after a sample was dispersed in phosphate-buffered saline. Specifically, relative activity with respect to initial activity of the enzyme-carrier complex of Example 1 using acylase and carbon nanotubes and the free acylase solution of Comparative Example 1 was evaluated for 200 days, and the results thereof are shown in FIG. 2.

Figure 2:
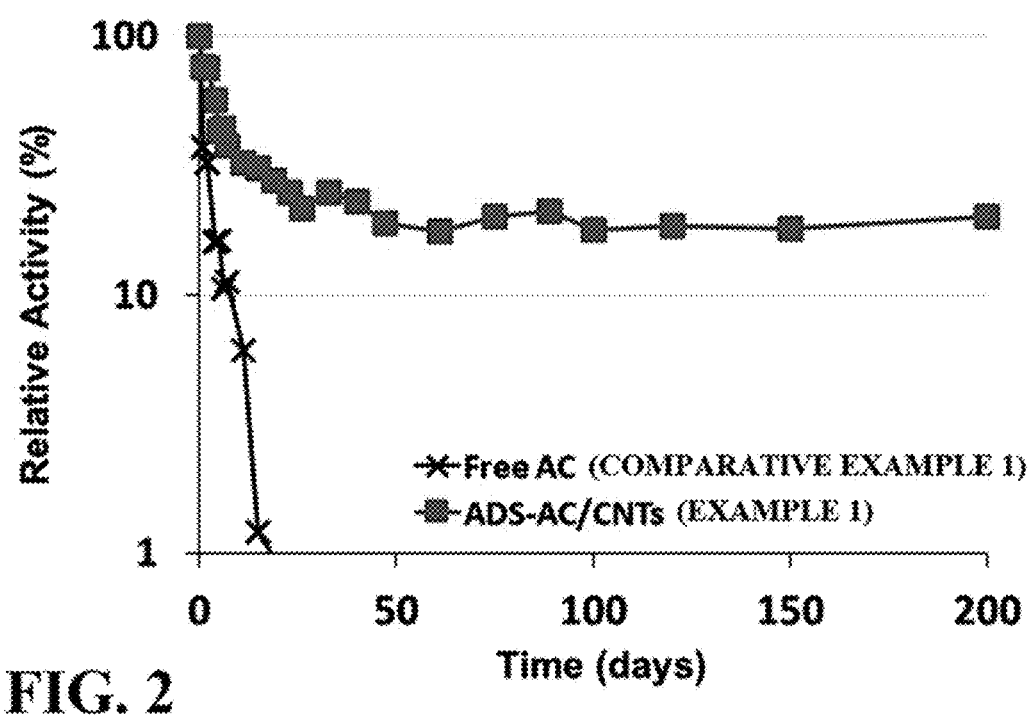
FIGS. 2 and 3 are graphs for evaluating enzyme stability by comparing an enzyme-carrier complex according to an embodiment of the present invention with an enzyme in a free state and each of enzyme-carrier complexes according to comparative examples.

As can be confirmed from FIG. 2, the enzyme in the case of Comparative Example 1 was non-activated within 19 days, whereas the case of Example 1 maintained a relative activity of 20% for 200 days. Specifically, the case of Example 1 exhibited a relative activity reduced to 23% for the first 40 days, and then stably maintained a relative activity of 23% until 200 days had elapsed.

Experimental Example 2

Figure 3:
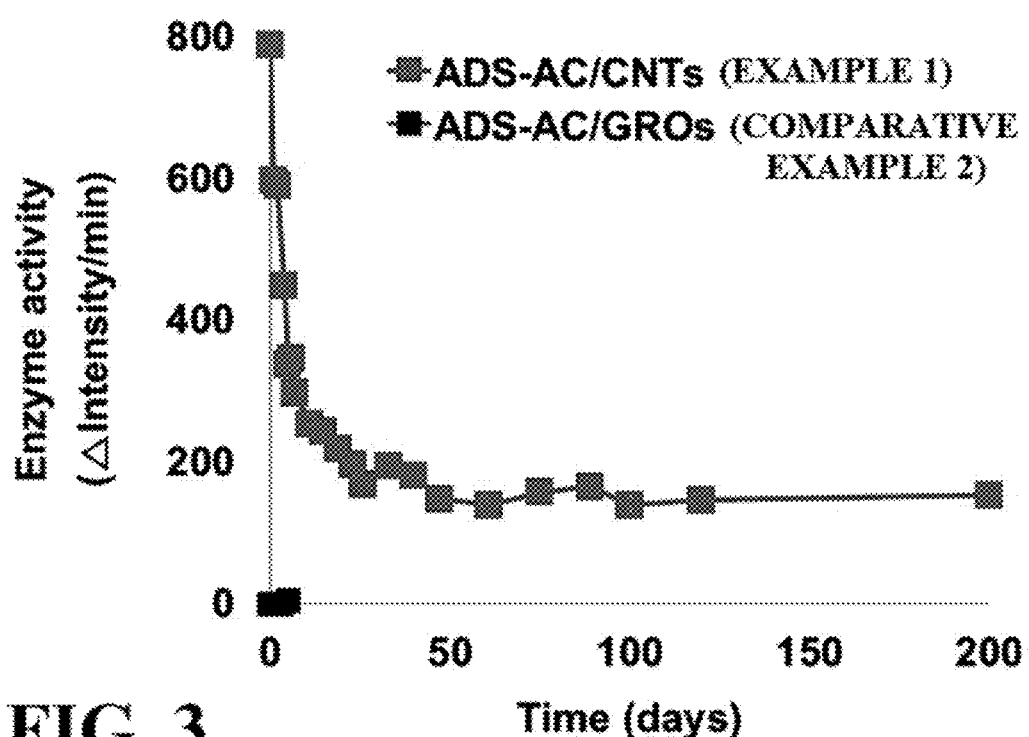

The enzymatic activity and stability of each of the enzyme-carrier complexes according to Example 1 and Comparative Example 2 were measured in the same manner as in Experimental Example 1, and the results thereof are shown in FIG. 3.

As can be confirmed from FIG. 3, the case of Example 1 maintained a relative activity of 20% for 200 days, whereas the case of Comparative Example 2 did not exhibit enzymatic activity after being immobilized.

<Comparative Example 3>—Carbon Nanotube (CNT) Solution

A solution in which carbon nanotubes (8 mg/mL) were added to phosphate-buffered saline (100 mM, pH 7.0) was prepared.

Experimental Example 3

Figure 4:
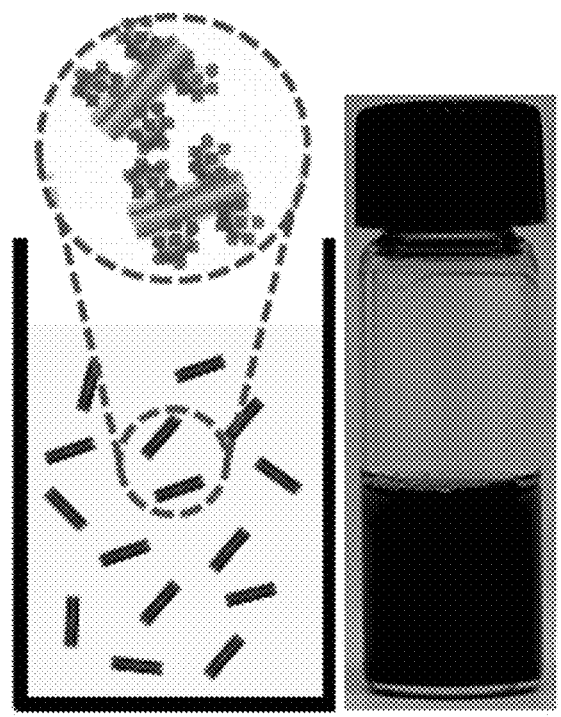
FIG. 4 illustrates an image and view showing a state in which an enzyme-carrier complex according to an embodiment of the present invention is dispersed in water.
Figure 5:
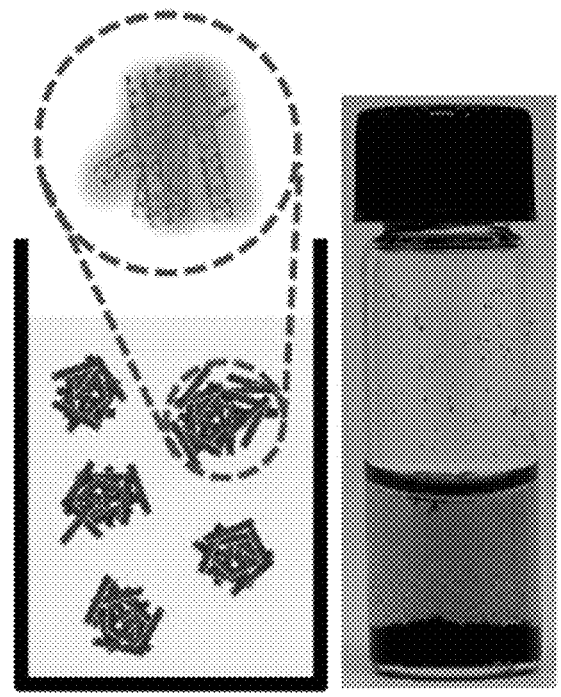
FIG. 5 illustrates an image and a view showing a state in which carbon nanotubes used as a carrier in the complex of FIG. 4 are dispersed alone in water.

Each of the enzyme-carrier complex according to Example 1 and the carbon nanotubes according to Comparative Example 3 was added to a water-containing container and stirred at 200 rpm for 1 hour, and then each container was left on a table for 1 minute, followed by photographing, and acquired images are shown in FIGS. 4 and 5.

As illustrated in FIG. 4, it can be confirmed that the enzyme-carrier complex of Example 1, in which acylase is adsorbed on surfaces of the carbon nanotubes, is uniformly dispersed in water, from which it can be seen that the enzyme-carrier complexes are not aggregated.

In contrast, as illustrated in FIG. 5, it can be confirmed that, when carbon nanotubes alone are dispersed in water, most settle on the bottom, and even when carbon nanotubes do not settle, the carbon nanotubes are present as grains aggregated therebetween.

The invention claimed is:

1. An enzyme-carrier complex comprising: a hydrophobic carrier which is a carbon nanotube; and one or more acylases adsorbed on a surface of the hydrophobic carrier, wherein the enzyme-carrier complex does not form aggregates in a dispersed state in water.

2. The enzyme-carrier complex of claim 1, wherein the hydrophobic carrier further comprises a first functional group on a surface thereof to induce a hydrophobic interaction with the enzyme.

3. The enzyme-carrier complex of claim 2, wherein the one or more acylases further comprises a second functional group for inducing a hydrophobic interaction with the first functional group.

4. The enzyme-carrier complex of claim 3, wherein the second functional group for inducing a hydrophobic interaction comprises one or more functional groups selected from the group consisting of a halogenated alkyl group, an organosilicon group, an alkyl group, a vinyl group, an allyl group, and an aryl group.

5. An electrode for a biofuel cell, the electrode comprising the enzyme-carrier complex according to claim 1.

6. An electrode for a biosensor, the electrode comprising the enzyme-carrier complex according to claim 1.

7. A carbon dioxide conversion system comprising the enzyme-carrier complex according to claim 1.

8. An antifouling system comprising the enzyme-carrier complex according to claim 1.

* * * * *